(12) United States Patent
Fredrickson

(10) Patent No.: US 7,060,319 B2
(45) Date of Patent: Jun. 13, 2006

(54) METHOD FOR USING AN ULTRASONIC NOZZLE TO COAT A MEDICAL APPLIANCE

(75) Inventor: Gerald Fredrickson, Westford, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

(21) Appl. No.: 10/670,819

(22) Filed: Sep. 24, 2003

(65) Prior Publication Data

US 2005/0064088 A1 Mar. 24, 2005

(51) Int. Cl.
*B05D 1/02* (2006.01)
*A61L 27/00* (2006.01)

(52) U.S. Cl. .................. 427/2.24; 427/2.28; 427/424; 427/600

(58) Field of Classification Search ........... 427/2.1, 427/2.24, 2.28, 421, 421.1, 424, 600, 182, 427/185, 422; 424/422, 424
See application file for complete search history.

(56) References Cited

U.S. PATENT DOCUMENTS

| | | | |
|---|---|---|---|
| 5,702,754 | A | 12/1997 | Zhong |
| 5,718,764 | A | 2/1998 | Walter |
| 6,270,801 | B1 | 8/2001 | Walter |
| 6,368,658 | B1 | 4/2002 | Schwarz et al. |
| 2002/0127327 | A1 | 9/2002 | Schwarz et al. |
| 2003/0165614 | A1 | 9/2003 | Hansen et al. |
| 2003/0230819 | A1 * | 12/2003 | Park et al. .................. 264/4 |

FOREIGN PATENT DOCUMENTS

EP 1 064 990 1/2001

OTHER PUBLICATIONS

CRITITECH: "Technology" Internet Article, Online Jun. 5, 2002, XP002312400 Retrieved from the Internet: <URL:http://www.crititech.com/technologh.html>retrieved on Jan. 3, 2005.
SONO-TEK: "Accu Mist—For Single Stent Coating Applications" Internet Article, Online Apr. 29, 2003, XP002312401 Retrieved from the Internet<URL:http://www.sono-tek.com/biomedical/accumist_stent.html> retrieved on Jan. 3, 2005.
Anonymous: "Cypher Stent Procedure" Internet Article, Online May 15, 2003, XP002312402 Retrieved from the Internet:,<URL:http://www.sip3d2.com/boh_1071/> retrieved on Jan. 4, 2005.
CritiTech website dated Jun. 15, 2002.*

* cited by examiner

*Primary Examiner*—Fred J. Parker
(74) *Attorney, Agent, or Firm*—Kenyon & Kenyon LLP (57) ABSTRACT

A method for coating a medical appliance includes suspending the medical appliance with a fluidizing gas flow and directing a coating onto an ultrasonic nozzle. The ultrasonic nozzle is directed towards the medical appliance. The method also includes vibrating the ultrasonic nozzle at a rate sufficient to atomize the coating. A device for coating a medical appliance includes a fluidizing gas source adapted to suspend the medical appliance in a suspension area and an ultrasonic nozzle directed at the suspension area and adapted to vibrate. The device also includes a coating source adapted to direct coating onto the ultrasonic nozzle. A medical appliance is provided which has a coating applied by the method.

16 Claims, 6 Drawing Sheets

METHOD FOR USING AN ULTRASONIC NOZZLE TO COAT A MEDICAL APPLIANCE

FIELD OF THE INVENTION

The present invention relates to the manufacturing of medical appliances. More particularly, the present invention relates to a device and method for coating medical appliances using an ultrasonic nozzle.

BACKGROUND INFORMATION

Medical devices may be coated so that the surfaces of such devices have desired properties or effects. For example, it may be useful to coat medical devices to provide for the localized delivery of therapeutic agents to target locations within the body, such as to treat localized disease (e.g., heart disease) or occluded body lumens. Localized drug delivery may avoid some of the problems of systemic drug administration, which may be accompanied by unwanted effects on parts of the body which are not to be treated. Additionally, treatment of the afflicted part of the body may require a high concentration of therapeutic agent that may not be achievable by systemic administration. Localized drug delivery may be achieved, for example, by coating balloon catheters, stents and the like with the therapeutic agent to be locally delivered. The coating on medical devices may provide for controlled release, which may include long-term or sustained release, of a bioactive material.

Aside from facilitating localized drug delivery, medical devices may be coated with materials to provide beneficial surface properties. For example, medical devices are often coated with radiopaque materials to allow for fluoroscopic visualization during placement in the body. It is also useful to coat certain devices to achieve enhanced biocompatibility and to improve surface properties such as lubriciousness.

Coatings have been applied to medical devices by processes such as dipping, spraying, vapor deposition, plasma polymerization, and electrodeposition. Although these processes have been used to produce satisfactory coatings, they have numerous, associated potential drawbacks. For example, it may be difficult to achieve coatings of uniform thicknesses, both on individual parts and on batches of parts. Also, these coating processes may require that the coated part be held during coating, which may result in defects such as bare spots where the part was held and which may thus require subsequent coating steps. Further, many conventional processes require multiple coating steps or stages for the application of a second coating material, or to allow for drying between coating steps or after the final coating step.

There is, therefore, a need for a cost-effective method of coating medical devices that results in uniform, defect-free coatings and uniform drug doses per unit device. The method would allow for a multiple stage coating in order to apply a bioactive material that may be environmentally sensitive, e.g., due to heat and light (including ultra-violet) exposure. Multiple stage coating may also be used to prevent degradation of the bioactive material due to process-related forces (e.g., shear). The method would thus allow for better control of the sensitivity of the bioactive material and reduce any potential degradation due to environmental issues. The method would also reduce variations in the coating properties.

Gas suspension coating is a process by which a large number of stents may be freely suspended in a nitrogen (or other) gas stream as a coating is applied and dried in one process. Two of the issues facing gas suspension are the effect of the process on the mechanical integrity of the stent and the effect on the coating.

One cause of damage to the stent and the coating in a gas suspension coating process is the velocity of the stent as it is fluidized. A gas suspension system utilizes a gas atomizing spray nozzle, which uses a jet of gas that can shoot stents at rapid speeds and can cause both coating and stent damage. This velocity can damage a stent and coating as the stent impacts other stents and the inside of the vessel. If this pressure could be reduced or eliminated then damage would be reduced or eliminated. These issues may become more critical with more flexible stent designs.

Current state of the art for gas suspension involves the use of a gas atomizing spray nozzle mounted at the base of a hurricade vessel. In order to obtain efficient coating it is necessary to mount the nozzle at the base to maximize the transfer of coating to the stents. One issue with mounting the spray nozzle at the base may be that the direction of the spray may be straight up. This direction is the same as that of the fluidization gas which suspends the stents. The atomization pressure may be highly focused and may tend to shoot the stents with high velocity when they pass over the spray nozzle.

There thus is a need for a method of coating stents in a gas suspension system that does not cause damage to the coating or stents.

SUMMARY OF THE INVENTION

According to an exemplary method of the present invention, stents are coated using an ultrasonic nozzle to atomize the coating while a fluidizing gas suspends the medical appliances. The fluidizing gas may also deliver the atomized coating from the ultrasonic nozzle to the medical appliances.

By using an ultrasonic coating nozzle, no atomizing pressure is required. This may eliminate the highly focused jet and the consequent shooting of stents at high velocity. There may be sufficient gas flow from the fluidization flow to distribute the atomized coating and keep the stents fluidized.

A method for coating a medical appliance includes suspending the medical appliance with a fluidizing gas flow and directing a coating onto an ultrasonic nozzle. The ultrasonic nozzle is directed towards the medical appliance. The method also includes vibrating the ultrasonic nozzle at a rate sufficient to atomize the coating. The method may also include directing a further gas flow at the ultrasonic nozzle. The further gas flow may transport the atomized coating to the at least one medical appliance. The method may also include directing the fluidizing gas flow at the ultrasonic nozzle. The fluidizing gas flow may transport the atomized coating to at least one medical appliance. The rate of vibration of the ultrasonic nozzle may be between about 48 kilohertz and about 122 kilohertz. The method may also include heating or cooling the fluidizing gas flow. The coating may include a therapeutic agent. The medical appliance may include a stent. The method may be used to coat between 200 and 600 stents. The stent may be a flexible stent. The operation of directing the coating onto the ultrasonic nozzle may include causing a flow of the coating of about 0.5 milliliters per minute. The operation of suspending the medical appliance with a fluidizing gas flow may be performed in a hurricade. The ultrasonic nozzle may be directed to the interior of the hurricade.

A device for coating a medical appliance includes a fluidizing gas source adapted to suspend the medical appliance in a suspension area and an ultrasonic nozzle directed at the suspension area and adapted to vibrate. The device also includes a coating source adapted to direct coating onto the ultrasonic nozzle. The nozzle is adapted to vibrate at a rate sufficient to atomize the coating. The device also may include a further gas source adapted to direct the atomized coating at the suspension area. The device also may include a hurricade enclosing the suspension area.

A medical appliance is provided which has a coating applied by a method which includes suspending the medical appliance with a fluidizing gas flow and directing a coating onto an ultrasonic nozzle. The ultrasonic nozzle is directed towards the medical appliance. The method also includes vibrating the ultrasonic nozzle at a rate sufficient to atomize the coating. The medical appliance may also be made by a method which may also include directing a further gas flow at the ultrasonic nozzle. The further gas flow may transport the atomized coating to the medical appliance. The medical appliance may also be made by a method which may also include directing the fluidizing gas flow at the ultrasonic nozzle. The fluidizing gas flow may transport the atomized coating to the medical appliance.

DETAILED DESCRIPTION

A major source of medical appliance velocity, and consequent medical appliance damage, during coating in an airstream coater is due to excessive gas velocity used to atomize the coating. The problem of damage to medical appliances during coating in an airstream coater due to excessive gas velocity may be eliminated if a different, less forceful, method of atomizing the coating is used. If the gas atomizing nozzle is replaced with an ultrasonic nozzle, which uses no gas pressure for atomization, then a major source of stent velocity may be eliminated. An ultrasonic atomizing nozzle may not require a jet of atomizing gas and, therefore, this type of coating system may be compatible with coating delicate items such as stents.

Figure 1:
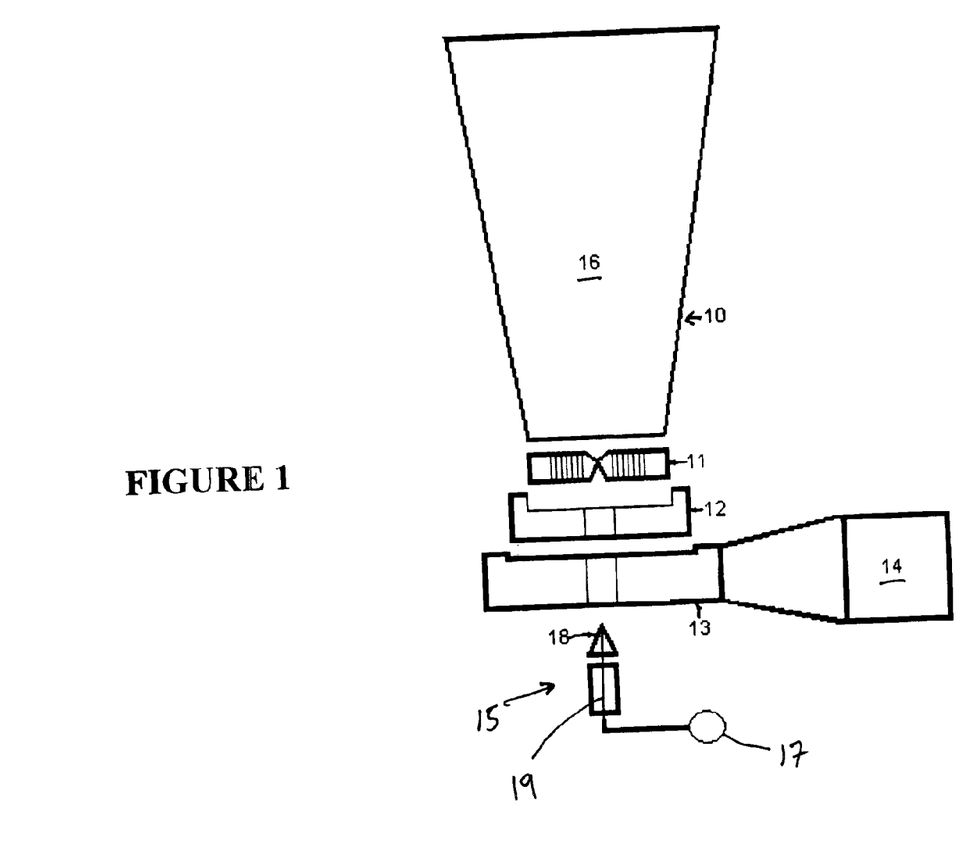
FIG. 1 shows an exploded view of a hurricade including an atomizing gas nozzle.

FIG. 1 shows hurricade 10 including atomizing gas nozzle 15. Positioned at the base of hurricade 10 is rotonozzle 11. Rotonozzle 11 may operate to cause the fluidizing gas flow to rotate or move in a particular manner, for instance in a particular direction or with a particular velocity. Rotonozzle 11 may also function to prevent any medical appliances from falling into any of the lower parts of the device in the event that the fluidizing gas is terminated or weakened. Rotonozzle 11 may include a screen having spaces alternating with solid material, and may also include slots, grooves or tubes, in any appropriate angle or orientation.

Below rotonozzle 11 is centering plate 12, which may operate to orient and connect fluidization plenum 13 with hurricade 10 via rotonozzle 11. Fluidization plenum 13 is arranged below centering plate 12. Fluidization plenum 13 is in fluid communication with fluidization gas source 14. Fluidization gas source 14 provides gas to fluidization plenum 13 at a pressure and velocity that is sufficient to maintain one or more medical appliances suspended in hurricade 10, and specifically in suspension region 16 of hurricade 10. Fluidization gas source 14 may provide pressurized gas that is free of particulate matter, and in particular may provide nitrogen, argon, air, or any other appropriate gas. Additionally, fluidization gas source 14 may heat or cool the gas prior to providing it to fluidization plenum 13. Suspension region 16 may include the entire region defined by the cone of hurricade 10, and may in particular include the region out to the walls of hurricade 10, down to rotonozzle 11 and up to or above the top edge of the cone of hurricade 10. Medical appliances, such as stents, may be suspended in a localized region of suspension region 16 or may drift around throughout the entire region of suspension region 16, and may even contact the walls of hurricade 10 and/or rotonozzle 11. The movement of medical appliances that are suspended in suspension region 16 may depend on the velocity and pressure of the pressurized gas provided by fluidization gas source 14, as well as the variation in this velocity and pressure over time, the number of medical appliances in hurricade 10, and any number of additional factors.

Gas atomizing spray nozzle 15 is shown in an exploded view below fluidization plenum 13. Gas atomizing spray nozzle 15 may operate in the following manner. Central tube 19 of gas atomizing spray nozzle 15 may carry fluid at a low pressure from coating source 17 to nozzle tip 18. Central tube 19 may carry the fluid from coating source 17 at a rate of 0.5 ml/minute. Surrounding central tube 19 at the nozzle tip is a high pressure gas source, which may be concentric with central tube 19. The high pressure gas may be at a pressure of greater than 20 psi (pounds per square inch), and may in particular be at a pressure of 35 psi. The high pressure gas atomizes the fluid exiting central tube 19 at nozzle tip 18. The fluid may be atomized to a drop size of 4–20 microns. The high pressure gas may carry the atomized fluid up through fluidization plenum 13, through centering plate 12, through rotonozzle 11, into hurricade 10, where it may be deposited on a medical appliance which is suspended in suspension region 16. This high pressure gas carrying atomized fluid may be traveling at a higher velocity and/or at a higher pressure than the gas from fluidization gas source 14. The high pressure gas carrying the atomized fluid may cause a medical appliance in suspension region 16 to move and impact a top above hurricade 10 or the wall of hurricade 10.

Figure 2:
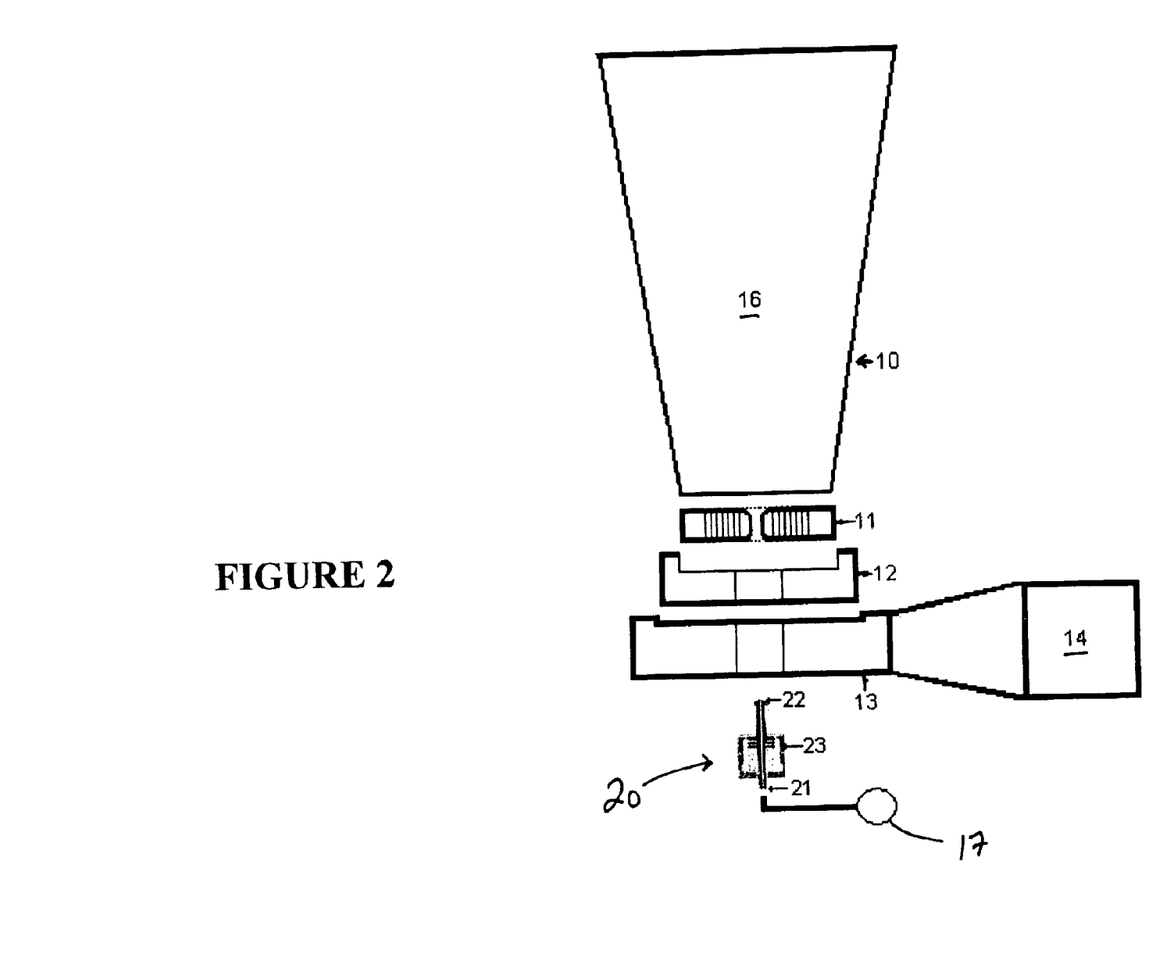
FIG. 2 shows an exploded view of an exemplary embodiment of the present invention including a hurricade and an ultrasonic nozzle.

FIG. 2 shows an exemplary embodiment of the present invention including hurricade 10 and ultrasonic gas nozzle 20. Hurricade 10 is situated above rotonozzle 11 which is situated above centering plate 12. Rotonozzle 11 and centering plate 12 may perform the same function as that described with respect to FIG. 1. Fluidization plenum 13 is situated below centering plate 12. Fluidization gas source 14 is in fluid communication with fluidization plenum 13. The high pressure gas provided by fluidization gas source 14 may be directed into the interior of hurricade 10 via fluidization plenum 13, centering plate 12 and rotonozzle 11. The high pressure gas may suspend medical appliances in suspension region 16 of hurricade 10. Ultrasonic nozzle 20 is shown in FIG. 2 in an exploded view.

Ultrasonic nozzle 20 may be in fluid communication with coating source 17 via tube 21. Ultrasonic nozzle 20 may include ultrasonic nozzle tip 22 and reciprocator 23. Ultrasonic nozzle tip 22 may extend into fluidization plenum 13 when it is in an assembled state. Ultrasonic nozzle 20 may operate in the following manner. Coating source 17 may be pressurized to cause coating to travel up tube 21. Alternatively, a pump may be situated between coating source 17 and tube 21. In another exemplary embodiment, coating source 17 may normally be pressurized, and a valve may be arranged between coating source 17 and tube 21 and may open when a coating operation is performed. The coating flows out onto the surface of ultrasonic nozzle tip 22 after reaching ultrasonic nozzle tip 22. Reciprocator 23 operates to move ultrasonic nozzle 20, and in particular ultrasonic nozzle tip 22, at a high rate of speed in an up and down direction. This vibration may occur at a high frequency, and in particular may occur at a frequency between about 48 kilohertz and about 122 kilohertz. The coating that is forced out of ultrasonic nozzle tip 22 and which flows onto the surface of ultrasonic nozzle tip 22 is therefore subject to this high speed vibration. The high rate of vibration causes waves to form in the coating on ultrasonic nozzle tip 22. As these waves increase in size due to higher vibration speeds, higher vibration amplitudes, and/or constructive interference with other waves of coating, some or all of the waves may become unstable. Unstable wave conditions in the coating may lead to a wave collapse, which may cause the atomization of some or all of the coating which formed the wave prior to collapse. This atomized coating may then be directed away from the surface of the coating on ultrasonic nozzle tip 22. The atomized coating may be carried by the pressurized air from fluidization gas source 14 up into hurricade 10.

Figure 3:
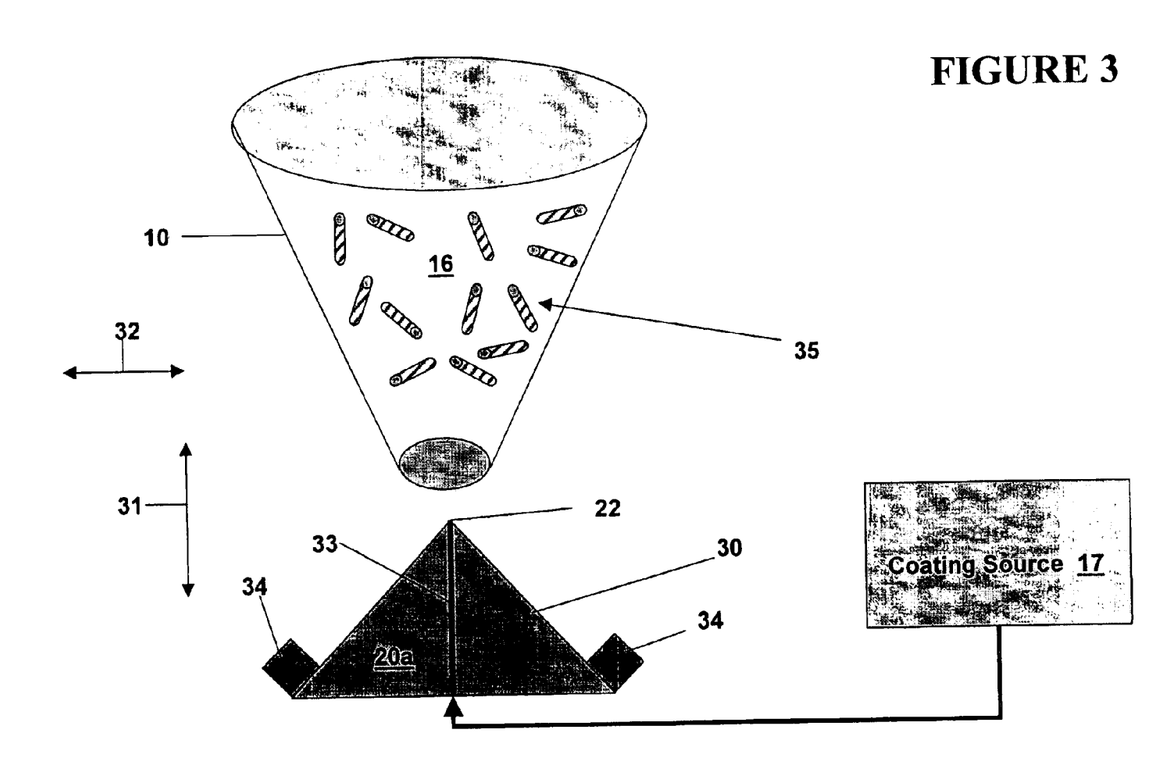
FIG. 3 shows a close-up view of an ultrasonic nozzle used in an exemplary embodiment of the present invention.

FIG. 3 shows ultrasonic nozzle 20 used in an exemplary embodiment of the present invention. Ultrasonic nozzle 20 is positioned in the same position as ultrasonic nozzle 20 of FIG. 2, namely at the base of hurricade 10. Ultrasonic nozzle 20 is shown in a close-up view (not to scale) and shows central tube 33, ultrasonic nozzle tip 22 and ultrasonic nozzle surface 30. As coating flows from coating source 17 to ultrasonic nozzle 20, the coating flows through central tube 33 of ultrasonic nozzle 20 up to ultrasonic nozzle tip 22. The coating then flows out of ultrasonic nozzle tip 22 thereby coating ultrasonic nozzle surface 30. Ultrasonic nozzle 20 vibrates at a high rate of speed in the direction of arrow 31 when operating. Alternatively, ultrasonic nozzle 20 may vibrate in a direction of arrow 32, which is perpendicular to arrow 31, or in any other direction. As discussed above, this vibration may occur at a high rate of speed, and in particular may occur at a rate between about 48 kilohertz and about 122 kilohertz. The coating covering ultrasonic nozzle surface 30 may form waves which propagate. These waves may interact with surface barriers 34 arranged at the outer edge of ultrasonic nozzle surface 30 and be reflected. As the waves of coating increase in size due to increased frequency and/or amplitude of the vibration, the waves will interfere with each other. When waves constructively interact, the energy of the wave may exceed a stability limit that may be dependent on the viscosity of the fluid, as well as other factors. When the stability limit on a wave is exceeded, the wave may collapse, which may cause the atomization of some or all of the coating material which constituted the wave. The atomized droplets created by ultrasonic nozzle 20 may be on the order of 10–15 microns. This atomized coating may then be transported to suspension region 16, where it may contact a surface of one or more of medical appliances 35 suspended in suspension region 16. After contacting a surface of one or more medical appliances 35, the coating may remain in place and be dried by the flow of the fluidizing gas.

Figure 4:
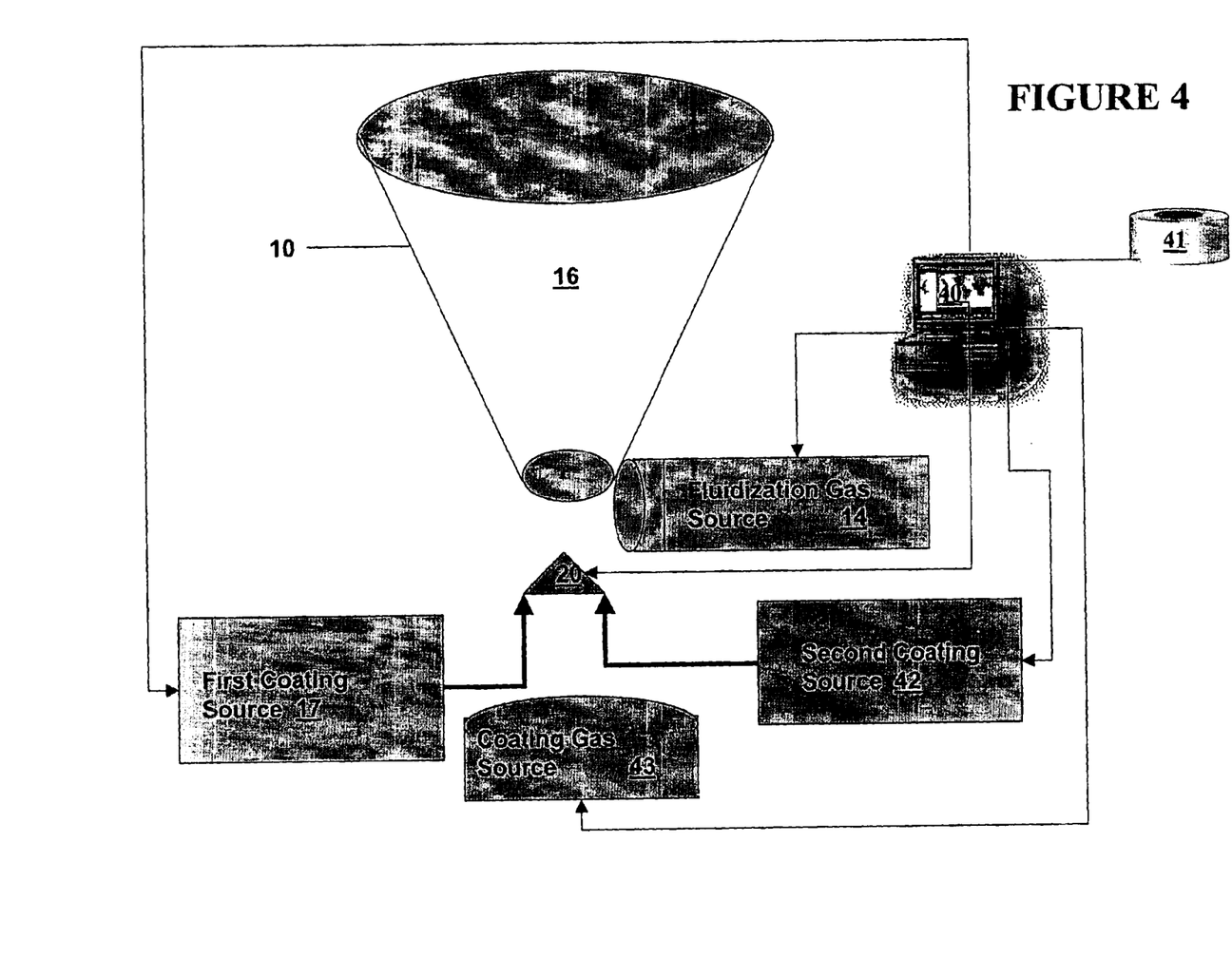
FIG. 4 shows a system for operating an exemplary embodiment of the present invention.

FIG. 4 shows a system for operating an exemplary embodiment of the present invention. Processor 40, which may be a computer, accesses memory 41, which may be integrated in processor 40 or may constitute a separate unit. Memory 41 holds instructions for operating some or all elements of the coating system. Additionally, processor 40 may include a manual interface, such as a keyboard, touchscreen, joystick or other arrangement for inputting instructions for operating the system. Processor 40 may be electrically coupled to any or all of first coating source 17, ultrasonic nozzle 20, fluidization gas source 14, and second coating source 42. Processor 40 may instruct first coating source 17 and/or second coating source 42 when to provide coating material to ultrasonic nozzle 20 and at what rate. Processor 40 may instruct ultrasonic nozzle 20 when to operate and at what rate of reciprocation. Processor 40 may also instruct fluidization gas source 14 when to operate, at what pressure and/or velocity to deliver air to a fluidization plenum, and at what temperature the gas should be.

Second coating source 42 may include a second coating for a medical appliance, which may be applied in consecutive fashion, alternating fashion, or simultaneously with the first coating. The instructions stored in memory 41 may be dependent on the number and type of medical appliances to be coated in either a batch or continuous processing system. These instructions may also depend on the type of coating and the intended use of the medical appliance. Variable quantities which may be determined by the type of coating operation may be input by a user into processor 40 to determine which instructions stored in memory 41 should be used in the coating operation.

Processor 40 may also control coating gas source 43. Coating gas source 43 may provide a flow of gas for carrying atomized coating from ultrasonic nozzle 20 to suspension region 16.

Figure 5:
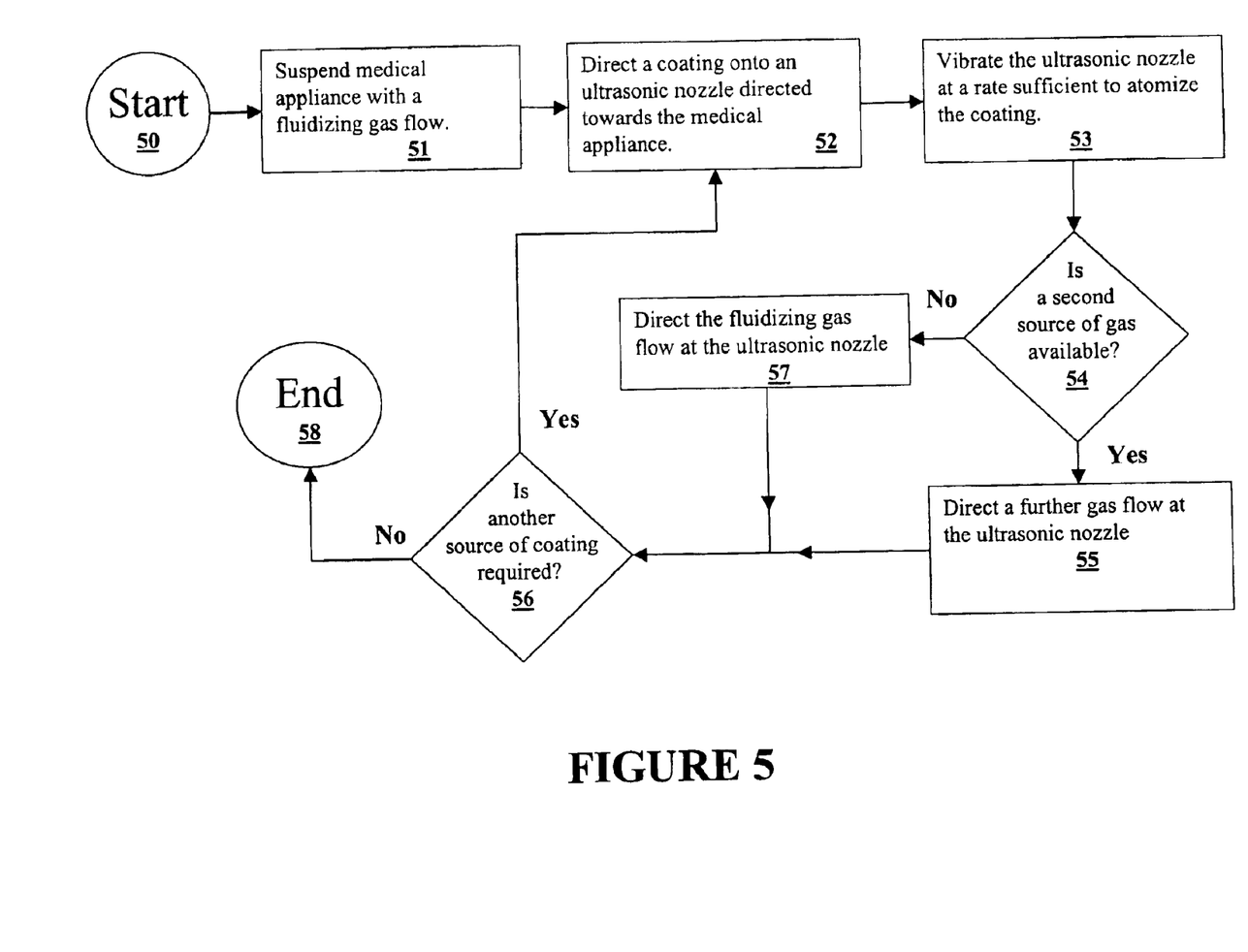
FIG. 5 shows a flowchart illustrating an exemplary method according to the present invention.

FIG. 5 shows a flowchart illustrating an exemplary method according to the present invention. The flow starts at start circle 50 and proceeds to action 51, which indicates to suspend a medical appliance with a fluidizing gas flow. From action 51 the flow proceeds to action 52, which indicates to direct a coating onto an ultrasonic nozzle directed towards the medical appliance. From action 52 the flow proceeds to action 53, which indicates to vibrate the ultrasonic nozzle at a rate sufficient to atomize the coating. From action 53 the flow proceeds to question 54, which asks whether a second source of gas is available. If the answer to question 54 is affirmative, the flow proceeds to action 55, which indicates to direct the further gas flow at the ultrasonic nozzle. From action 55 the flow proceeds to question 56, which asks whether another source of coating is required. If the answer to question 56 is affirmative, the flow proceeds back to action 52. If the answer to question 54 is negative, the flow proceeds to action 57, which indicates to direct the fluidizing gas flow at the ultrasonic nozzle. From action 57 the flow proceeds to question 56. If the answer to question 56 is negative, the flow proceeds to end circle 58.

Figure 6:
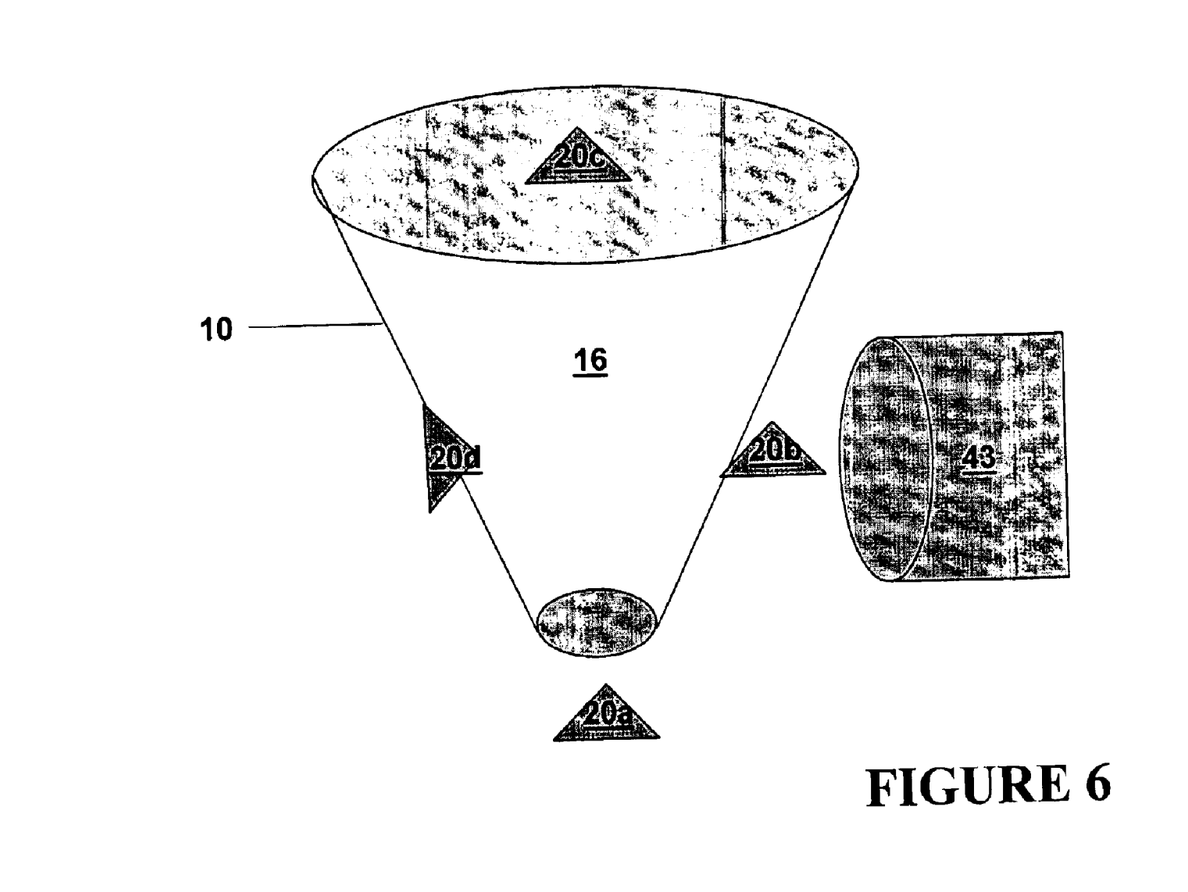
FIG. 6 shows an exemplary embodiment of the present invention showing a hurricade with various positions for an ultrasonic nozzle and gas source.

FIG. 6 shows a hurricade with various positions for ultrasonic nozzles 20a, 20b, 20c, 20d used in an exemplary embodiment of the present invention. Ultrasonic nozzle 20a may be positioned at the base of hurricade 10. Ultrasonic nozzle 20b may be positioned on the side of hurricade 10. Ultrasonic nozzle 20c may be positioned on the top of hurricade 10. Ultrasonic nozzle 20d may be positioned on the side of hurricade 10 and oriented at 90 degrees so that the surface of ultrasonic nozzle 20*d* faces suspension region 16 in the center of hurricade 10. Additionally, ultrasonic nozzles 20*a* and 20*c* may be oriented at 90 degrees, and additionally, all of ultrasonic nozzles 20*a*, 20*b*, 20*c*, 20*d* may be oriented at various other directions. Ultrasonic nozzles 20*a*, 20*b*, 20*c*, 20*d* may be used as alternative positions for a single ultrasonic nozzle used with hurricade 10. Alternatively, two or more of ultrasonic nozzles 20*a*, 20*b*, 20*c*, 20*d* may be used in conjunction with hurricade 10.

There are at least three possible variations of the design of the hurricade. First, the nozzle may be mounted at the base of the hurricade with the tip facing up into the hurricade. Second, the nozzle may be mounted through the side of the hurricade with the tip inserted through a side port and being centered in the diameter of the cross section of the vessel. Third, the nozzle could be mounted through the top of the hurricade vessel with the tip centered in the top and protruding down to the base of the hurricade. The nozzle may be most effective if mounted from the bottom or side where the tip could be placed closest to the vessel base.

Coating gas source 43 is shown directed at ultrasonic nozzle 20*b* and may provide low pressure and/or low velocity gas for transporting the atomized coating to suspension region 16 of hurricade 10. Alternatively, coating gas source 43 may be positioned adjacent to any of ultrasonic nozzles 20*a*, 20*c*, 20*d*. There may be multiple coating gas sources 43 for a single one of ultrasonic nozzles 20*a*, 20*b*, 20*c*, 20*d* and/or multiple coating gas sources 43 for multiple ultrasonic nozzles.

Ultrasonic nozzles 20*a*, 20*b*, 20*c*, 20*d* may be made of any acceptable material, including materials which are currently used for ultrasonic nozzles. For instance, the materials may be solvent resistant and may include metals such as stainless steel and titanium. The remainder of the gas suspension equipment may be constructed of any appropriate material, including materials which are currently used, such as stainless steel. A commercially available ultrasonic nozzle may be fitted to an existing gas suspension unit. Modifications to the unit may be made.

Medical implants are used for innumerable medical purposes, including the reinforcement of recently re-enlarged lumens, the replacement of ruptured vessels, and the treatment of disease such as vascular disease by local pharmacotherapy, i.e., delivering therapeutic drug doses to target tissues while minimizing systemic side effects. Such localized delivery of therapeutic agents has been proposed or achieved using medical implants which both support a lumen within a patient's body and place appropriate coatings containing absorbable therapeutic agents at the implant location. Examples of such medical devices include catheters, guide wires, balloons, filters (e.g., vena cava filters), stents, stent grafts, vascular grafts, intraluminal paving systems, implants and other devices used in connection with drug-loaded polymer coatings. Such medical devices are implanted or otherwise utilized in body lumina and organs such as the coronary vasculature, esophagus, trachea, colon, biliary tract, urinary tract, prostate, brain, and the like.

The term "therapeutic agent" as used herein includes one or more "therapeutic agents" or "drugs". The terms "therapeutic agents" and "drugs" are used interchangeably herein and include pharmaceutically active compounds, nucleic acids with and without carrier vectors such as lipids, compacting agents (such as histones), viruses (such as adenovirus, andenoassociated virus, retrovirus, lentivirus and α-virus), polymers, hyaluronic acid, proteins, cells and the like, with or without targeting sequences.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; anti-proliferative agents such as enoxaprin, angiopeptin, rapamycin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Coatings used with the present invention may comprise a polymeric material/drug agent matrix formed, for example, by admixing a drug agent with a liquid polymer, in the absence of a solvent, to form a liquid polymer/drug agent mixture. Curing of the mixture typically occurs in-situ. To facilitate curing, a cross-linking or curing agent may be added to the mixture prior to application thereof. Addition of the cross-linking or curing agent to the polymer/drug agent liquid mixture must not occur too far in advance of the application of the mixture in order to avoid over-curing of the mixture prior to application thereof. Curing may also occur in-situ by exposing the polymer/drug agent mixture, after application to the luminal surface, to radiation such as ultraviolet radiation or laser light, heat, or by contact with metabolic fluids such as water at the site where the mixture has been applied to the luminal surface. In coating systems employed in conjunction with the present invention, the polymeric material may be either bioabsorbable or biostable. Any of the polymers described herein that may be formulated as a liquid may be used to form the polymer/drug agent mixture.

In an exemplary embodiment, the polymer used to coat the medical device is provided in the form of a coating on an expandable portion of a medical device. After applying the drug solution to the polymer and evaporating the volatile solvent from the polymer, the medical device is inserted into a body lumen where it is positioned to a target location. In the case of a balloon catheter, the expandable portion of the catheter is subsequently expanded to bring the drug-impregnated polymer coating into contact with the lumen wall. The drug is released from the polymer as it slowly dissolves into the aqueous bodily fluids and diffuses out of the polymer. This enables administration of the drug to be site-specific, limiting the exposure of the rest of the body to the drug.

The polymer used in the present invention is preferably capable of absorbing a substantial amount of drug solution. When applied as a coating on a medical device in accordance with the present invention, the dry polymer is typically on the order of from about 1 to about 50 microns thick. In the case of a balloon catheter, the thickness is preferably about 1 to 10 microns thick, and more preferably about 2 to 5 microns. Very thin polymer coatings, e.g., of about 0.2–0.3 microns and much thicker coatings, e.g., more than 10 microns, are also possible. It is also within the scope of the present invention to apply multiple layers of polymer coating onto a medical device. Such multiple layers are of the same or different polymer materials.

The polymer of the present invention may be hydrophilic or hydrophobic, and may be selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHDROL®, etc.) and acrylic latex dispersions are also within the scope of the present invention. The polymer may be a protein polymer, fibrin, collagen and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment of the invention, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference. U.S. Pat. No. 5,091,205 describes medical devices coated with one or more polyisocyanates such that the devices become instantly lubricious when exposed to body fluids. In another preferred embodiment of the invention, the polymer is a copolymer of polylactic acid and polycaprolactone.

While the present invention has been described in connection with the foregoing representative embodiment, it should be readily apparent to those of ordinary skill in the art that the representative embodiment is exemplary in nature and is not to be construed as limiting the scope of protection for the invention as set forth in the appended claims.

What is claimed is:

1. A method for coating at least a portion of at least one medical appliance, comprising:
    suspending the at least one medical appliance in a fluidizing gas flow;
    directing a coating onto an ultrasonic nozzle, the ultrasonic nozzle directed towards the at least one medical appliance; and
    vibrating the ultrasonic nozzle at a rate sufficient to atomize the coating.

2. The method of claim 1, further comprising directing a further gas flow at the ultrasonic nozzle, the further gas flow transporting the atomized coating to the at least one medical appliance.

3. The method of claim 1, further comprising directing the fluidizing gas flow at the ultrasonic nozzle, the fluidizing gas flow transporting the atomized coating to the at least one medical appliance.

4. The method of claim 1, wherein the rate of vibration of the ultrasonic nozzle is between about 48 kilohertz and about 122 kilohertz.

5. The method of claim 4, wherein the rate of vibration of the ultrasonic nozzle is about 122 kilohertz.

6. The method of claim 1, further comprising one of heating and cooling the fluidizing gas flow.

7. The method of claim 1, wherein the coating includes a therapeutic agent.

8. The method of claim 1, wherein the at least one medical appliance includes at least one stent.

9. The method of claim 8, wherein the at least one stent includes between about 200 and about 600 stents.

10. The method of claim 8, wherein the at least one stent includes a flexible stent.

11. The method of claim 8, wherein the operation of directing the coating onto the ultrasonic nozzle includes causing a flow of the coating of about 0.5 milliliters per minute.

12. The method of claim 1, wherein the operation of suspending the at least one medical appliance with a fluidizing gas flow is performed in a hurricade.

13. The method of claim 12, wherein the ultrasonic nozzle is directed to the interior of the hurricade.

14. The method of claim 1, wherein the gas in the fluidizing gas flow is selected from the group of nitrogen, argon and air.

15. The method of claim 1, wherein the gas in the fluidizing gas flow is at a pressure of 35 psi.

16. The method of claim 1, wherein the gas in the fluidizing gas flow is at a pressure of greater than 20 psi.

* * * * *